US006970743B2

(12) United States Patent  
Weinberg et al.

(10) Patent No.: US 6,970,743 B2  
(45) Date of Patent: Nov. 29, 2005

(54) SYSTEM AND METHOD FOR TREATING ABNORMAL VENTRICULAR ACTIVATION-RECOVERY TIME

(75) Inventors: Lisa P. Weinberg, Moorpark, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 511 days.

(21) Appl. No.: 10/233,108

(22) Filed: Aug. 30, 2002

(65) Prior Publication Data

US 2004/0044374 A1 Mar. 4, 2004

(51) Int. Cl.[7] .............................................. A61N 1/362
(52) U.S. Cl. ........................................ 607/25; 607/9
(58) Field of Search ................................... 607/4–28

(56) References Cited

U.S. PATENT DOCUMENTS

| | | | | |
|---|---|---|---|---|
| 4,228,803 A | 10/1980 | Rickards | ..................... | 128/419 |
| 5,271,393 A | 12/1993 | Callaghan | ..................... | 607/14 |
| 5,419,338 A | 5/1995 | Sarma et al. | ................ | 128/703 |
| 5,476,483 A | 12/1995 | Bornzin et al. | ............... | 607/17 |
| 5,560,368 A | 10/1996 | Berger | ......................... | 128/703 |
| 5,560,370 A | 10/1996 | Verrier et al. | ............... | 128/705 |
| 5,842,997 A | 12/1998 | Verrier et al. | ............... | 600/518 |
| 5,861,011 A | 1/1999 | Stoop | .......................... | 607/25 |
| 5,902,250 A | 5/1999 | Verrier et al. | ............... | 600/515 |
| 5,921,940 A | 7/1999 | Verrier et al. | ............... | 600/518 |
| 6,058,328 A | 5/2000 | Levine et al. | ................. | 607/14 |
| 6,128,534 A * | 10/2000 | Park et al. | ..................... | 607/17 |
| 6,161,041 A | 12/2000 | Stoop et al. | ................... | 607/14 |
| 6,238,422 B1 * | 5/2001 | Van Oort | ...................... | 607/25 |
| 6,865,420 B1 * | 3/2002 | Kroll | ............................ | 607/25 |
| 6,370,431 B1 | 4/2002 | Stoop et al. | ................... | 607/14 |
| 2001/0007948 A1 | 7/2001 | Stoop et al. | ................... | 607/14 |

OTHER PUBLICATIONS

M.Chinushi et al., "Cycle Length-Associated Modulation of the Regional Dispersion of Ventricular Repolarization in a Canine Model of Long QT Syndrome," PACE, vol. 24, pp. 1247-1257 (Aug. 2001).

P.H. Chew et al. "Overnight Heart Rate and Cardiac Function in Patients with Dual Chamber Pacemakers," PACE, vol. 19, pp. 822-828 (May 1996).

M. Pye, et al., "QT Interval Dispersion: A Non-invasive Marker of Susceptibility to Arrhythmia in Patients With Sustained Ventricular Arrhythmias?" Br Heart J, 1994; 71:511-514.

P.D. Highham et al., "QT Dispersion,"Br Heart J, 1994; 71:508-510.

A.J. Moss et al., "Efficacy of Permanent Pacing in the Management of High-Risk Patients With Long QT Syndrome," Circulation, vol. 84, No. 4 (Oct. 1991).

(Continued)

Primary Examiner—Scott M. Getzow

(57) ABSTRACT

An implantable cardiac stimulation device provides long QT interval therapy for preventing abnormal ventricular activation-recovery time and ultimately ventricular arrhythmias. The device includes a sensing circuit that senses intracardiac activity of a heart and that generates electrical signals representing electrical activity of the heart. The device includes a physiologic sensor, such as body motion, or other diurnally varying sensor that reliably detects a diurnal state of the patient (i.e., not the QT interval itself). The device further includes a measuring circuit that measures a QT interval of the electrical signals, a control circuit that determines whether the QT interval is appropriate for the diurnal state, and a pulse generator that delivers pacing pulses to at least one chamber of the heart at a pacing rate when the QT Interval is pathologically too long. Furthermore, the pacing rate control circuit varies the pacing rate of the pulse generator responsive to the measured QT interval according to the measured diurnal state.

58 Claims, 12 Drawing Sheets

OTHER PUBLICATIONS

R.G. Weintraub et al., "The Congenital Long QT Syndromes in Childhood," JACC, vol. 16, No. 3, 674-80 (Sep. 1990).
*Cardiac Pacing, Electrophysiology, Tachyarrhythmias*, F.P. Gomez (Editor), Editorial Grouz, Madrid 1985.
S. Viskin M.D., "Cardiac Pacing in the Long QT Syndrome: Review of Available Data and Practical Recommendations," Journal of Cardiovascular Electrophysiology, vol. 11, No. 5 (May 2000).
M. Chinusi et al., "Activation-Recovery Interval as a Parameter to Assess the Intracardiac Ventricular Repolarization in Patients with Congenital Long QT Syndrome," the American Journal of Cardiology, vol. 90 (Aug. 15, 2002).
S. Viskin, et al., "Prevention of Torsade de Poniters in the Congenital Long QT Syndrome: Use of a Pause Prevention Pacing Algorithm," *Heart* 1998; vol. 79, pp. 417-419.
V. Pekarsky et al., "Prevention of Recurrent Life-Threatening Ventricular Arrhythmias by Temporary Cardiac Pacing," Acta Med Scand 1985, vol. 217, pp. 95-99.

J. Karjalkainen et al., "Relation Between QT Intervals and Heart Rates From 40 to 120 Beats/Min in Rest Electrocardiograms of Men and a Simple Method to Adjust QT Interval Values," JACC, vol. 23, No. 7, pp. 1547-1553 (Jun. 1994).
M.R. Franz, "Time for Yet Another QT Correction Alogrithm? Bazett and Beyond," Editorial Comment, JACC, vol. 23, No. 7, pp. 1554-1556 (Jun. 1994).
P. Puddu et al., "The QT-Sensitive Cybernetic Pacemaker: A New Role for an Old Parameter?" PACE, vol. 9, pp. 108-123 (Jan.-Feb. 1986, Part 1).
J.R. Milne et al., "The Ventricular Paced QT Interval —The Effects of Rate and Exercise," PACE, vol. 5, pp. 352-358 (May-Jun. 1982).
W. Gibb, et al., "An Alternative Method of Measuring the QT Interval," Europace 1997 Abstracts: 20, 1454.

* cited by examiner

SYSTEM AND METHOD FOR TREATING ABNORMAL VENTRICULAR ACTIVATION-RECOVERY TIME

FIELD OF THE INVENTION

The present invention generally relates to an implantable cardiac stimulation device, and more particularly relates to an implantable cardiac stimulation device capable of providing therapy to maintain a normal activation-recovery time, thereby preventing ventricular arrhythmias associated with Long QT Syndrome, Torsade de Pointe and ventricular fibrillation.

BACKGROUND OF THE INVENTION

Implantable cardiac stimulation devices are well known in the art. They may take the form of implantable defibrillators or cardioverters which treat accelerated rhythms of the heart, such as fibrillation, or implantable pacemakers which maintain the heart rate above a prescribed limit, such as, for example, to treat a bradycardia. Implantable cardiac devices are also known which incorporate both a pacemaker and a defibrillator.

As seen on a standard electrocardiogram (ECG), one complete heartbeat includes a P-wave, a QRS complex, and a T-wave. In a normal cardiac cycle, the atria depolarize and contract (P-waves), delivering blood into the relaxed ventricles. The atria now repolarize and relax while the ventricles, now filled to capacity with blood, depolarize, contract and pump (QRS complex) blood into the systemic and pulmonary circulation systems. The ventricles then repolarize and relax (T-wave). The cycle begins again at the end of ventricular repolarization with the onset of passive ventricular filling. The "QT" interval is measured from the onset of the QRS complex to the end of the visible T-wave on the surface ECG. The QT interval is generally accepted as an indirect measure of patient myocardial depolarization and repolarization. The QT interval prolongation may occur naturally during sleep, or by a variety of drugs, electrolyte imbalance, central nervous system disorders, metabolic abnormalities, bradycardia, ischemia and other intrinsic disease states.

The lengthening in the QT interval is associated with increased temporal dispersion of myocardial refractoriness which sets the stage for local reentry and initiation of life threatening ventricular arrhythmias, including Torsade de Pointe (TdP), ventricular fibrillation, often leading to syncope and sudden cardiac death. Of particular interest, the ventricular tachyarrhythmia known as Torsade de Pointe is unique: it is not a uniform shape, but shows a cyclic change in morphology in that the QRS complexes appear to be turning around a point.

For patients who develop acquired Long QT Syndrome (LQTS), the treatment typically is correction of the underlying metabolic abnormality or withdrawal from the medication that has initiated this problem. Until the problem is reversed, temporary cardiac pacing at a relative fast, fixed rate is commonly utilized to stabilize the rhythm and prevent the TdP. Sometimes, intravenous magnesium sulfate is also utilized.

There is also a condition known as Congenital LQTS. To date, five separate genetic abnormalities have been identified as causes of this condition in various individuals. Congenital LQTS is associated with sudden death in adolescents and young adults. Part of this syndrome involves an imbalance in the sympathetic neural innervation of the heart. Hence, one approach to treating this condition is the use of beta adrenergic receptor blocking drugs (beta blockers) to correct the intrinsic imbalance of neural innervation to the heart. However, this is associated with further slowing of the heart rate, which has a negative effect of lengthening the QT interval.

In patients with congenital LQTS whose heart rate has slowed with beta blockers or who have been shown to have a significant shortening of their QT interval with higher heart rates, permanent pacing has been used. In this setting, the base rate of the pacemaker is set to a fixed rate of about 80 or 90 bpm. Unfortunately, there is also evidence that pacing at a relatively high rate may be associated with progressive ventricular dysfunction. It is known, for example, that intrinsic sustained or incessant tachycardias may cause a cardiomyopathy. Hence, keeping the heart rate elevated at such a fixed rate, and never allowing it to decrease in accordance with a physiologic diurnal variation, may be counterproductive on a long term basis.

It is also known that QT interval varies diurnally, having a first level during the daytime and a second level during sleep associated with, but independent of, a slower heart rate. The QT interval is further known to shorten due to exercise, and circulating catecholamines, and further shortens due to increased heart rates. These fluctuations make it an unattractive sensor to be used alone for predicting the patient's vulnerability to tachyarrhythmias. For example, U.S. Pat. No. 6,370,431 suggests that "QT prolongation by itself is likely, for most patients, to be an insufficient predictor of the true onset of TdP or another ventricular arrhythmia", and instead seeks to find secondary indicators to predict true onset.

It is also known that there is a higher incidence of tachyarrhythmias in the early morning hours, which may be due to the inability of the patient's heart to resume a normal QT interval upon wakening. Couple this condition with premature ventricular beats that may arise due to the changes in activation-recovery states of the tissue, and the stage is set for VT, VF and sudden cardiac death.

As mentioned above, the QT interval has been used to detect sleep-wake states (see for example, U.S. Pat. No. 5,861,011, Stoop). However, in patients with abnormally long QT intervals and LQTS, monitoring the QT interval by itself may not be an accurate or reliable indicator of sleep-wake states. Furthermore, it is reported that the QT interval is believed to be unreliable in the presence of bundle branch block.

Rate smoothing is a mode of pacing that has used to prevent the relative bradycardia associated with the pauses, which follow a premature ventricular contraction (PVC). This relative bradycardia has also been shown to exacerbate the QT interval lengthening and results in a worsening of the arrhythmias.

Where pacing is not totally effective, or there is a history of sudden death in family members, an increasing number of physicians are recommending an implantable cardioverter defibrillator (ICD). While an ICD provides absolute rescue therapy, it is painful. In addition, if the ICD is used to provide high rate bradycardia pacing, this will significantly shorten the projected longevity of the ICD.

Hence, there is a need in the art for a more effective treatment of abnormally long QT interval such as that associated with LQTS. The present invention provides an implantable cardiac stimulation device capable for providing such therapy.

SUMMARY OF THE INVENTION

The present invention therefore provides an implantable cardiac stimulation device capable of detecting a lengthening in the QT interval associated with pathological ventricular activation-recovery properties (i.e., not associated with a physiologic need or normal exercise response and recovery) that may be a precursor to Long QT Syndrome (LQTS), Torsade de Pointe (TdP), ventricular fibrillation, syncope and/or sudden cardiac death. The present invention then provides preventative pacing therapy to alter and remodel the ventricular activation-recovery properties by increasing the pacing rate so that the QT interval is maintained within a normal range for the patient's diurnal state.

Accordingly, in a first embodiment, the present invention utilizes a diurnal sensor to determine a diurnal state of the patient (e.g., at least sleep and awake states). A lengthening of the QT interval in excess of an expected threshold for each diurnal state provides a first indication that the QT interval is abnormally long. Thus, when the diurnal sensor indicates that the patient is no longer sleeping, the QT interval is continuously maintained in a normal range for the early morning hours, when the patient is most at risk for a tachyarrhythmia.

The present invention can further utilize the diurnal sensor to determine or learn a daytime and a sleep time normal range for the QT interval and allow the patient's heart rate (corresponding to a longer QT interval) to slow at night, thus maintaining a normal heart rate pattern diurnally.

In a second embodiment, the present invention ensures that false positive indicators are minimized. For example, a loss of capture may falsely indicate an abnormal QT interval. In this embodiment, the present invention may verify capture in one or both ventricular chambers of the patient's heart to ensure that a lengthening of the QT interval is not due to a loss of capture. If a loss of capture is present, the present invention can re-establish capture before evaluating the QT interval for abnormal activation-recovery properties of the patient's heart.

An inappropriate V—V timing delay may also falsely indicate an abnormal QT interval. In this embodiment, the present invention may further analyze the V—V timing of the patient's heart to ensure that a lengthening of the QT interval is not due to an inappropriate conduction delay between two chambers of the heart. Thus, the present invention can adjust V—V timing before evaluating the QT interval for abnormal activation-recovery properties of the patient's heart.

As used herein, the QT interval includes both the "QRS" (or depolarization) portion and the T-wave (or repolarization) portion of the ventricular signal, either spontaneous or evoked by pacing. The QT interval may also be associated with one of the ventricles (e.g., left or right), or the difference between the left and right ventricles of the heart. As used herein, LQTS includes both the congenital and the acquired LQTS.

Accordingly, the device comprises a sensing circuit that senses intracardiac activity of a heart and generates electrical signals representing electrical activity of the heart. From the electrical signals a measuring circuit measures a QT interval. The device further comprises a pulse generator that delivers pacing pulses to at least one chamber of the heart at an adjustable pacing rate, and a pacing rate control circuit that varies the pacing rate to maintain the measured QT interval (QTI) in an acceptable normal range, defined either by the physician, or automatically determined by the device by averaging daytime and night time QT intervals.

More specifically with regard to rate control, it is known with rate responsive "QT pacemakers" that the "QT interval" shortens due to exercise while in the presence of bradycardia, thereby indicating the need to increase the pacing rate by the device. However, an increase in the pacing rate will also shorten the measured QT interval. It is this phenomenon (i.e., positive feedback) that also prohibits the QT rate-responsive pacemakers from operating in a closed-loop fashion. For rate responsive control, the rate must be "corrected" for this added shortening of the QT interval.

The present invention takes advantage of this latter phenomenon when used as the control parameter for pathological lengthening of the QT interval. That is, regardless of whether the patient has a gradual or sudden lengthening of the QT interval, the present invention can monitor any abnormal QT interval change and increase the pacing rate to a value that is sufficient to overcome the abnormal QT interval (i.e., by increasing the pacing rate, the QT interval shortens). Furthermore, the present invention maintains the elevated rate for a duration only necessitated by the patient's immediate QT needs, in a closed-loop (i.e., a negative feedback) fashion, thereby eliminating unnecessarily high fixed rates for extended periods of time.

The control circuit increases the pacing rate when a measured QT interval exceeds a predetermined expected value for the indicated diurnal state. In one embodiment, the present invention can learn the patient's normal QT interval for sleep and awake states by incorporating a diurnal sensor (e.g., a body motion sensor) to detect these states and then take an average measurement in those states as the baseline value.

The pulse generator may further be configured to deliver pacing pulses to one of the ventricles of the heart or to deliver bi-ventricular pacing pulses in order to resynchronize both ventricles of the heart, and therefore optimize activation-repolarization times that might otherwise be too long. The pulse generator may also be configured to deliver pacing pulses to an atrium of the heart, which results in an increase in heart rate that has the same effect of decreasing the QT interval.

The device may further comprise a data acquisition system, responsive to the electrical signals, that provides QT interval diagnostic data and a memory that stores the diagnostic data. The diagnostic data may include a histogram. The histogram may include a QT interval histogram, a separate stim-T interval histogram, or a J-T interval histogram. In one embodiment, these histogram data may also be obtained for sleep and wake states.

The diagnostic data may also include other pacing data, such as pacing rate and pacing status. The diagnostic data may also include date stamping so that a plot of QT interval values versus time may be obtained. The QT interval values versus time are preferably plotted over a last time period, which is reset table by the physician.

The invention further provides an implantable cardiac stimulation device comprising sensing means for sensing electrical activity of a heart and providing at least one electrogram signal, and stimulating means for providing pacing pulses to at least one chamber of the heart at a pacing rate. The device further comprises pacing rate control means responsive to a QT interval in the electrogram signal for varying the pacing rate in a closed loop fashion in the presence of abnormally long QT intervals associated with, for example, Long QT Syndrome.

The present invention still further provides a method for use in an implantable cardiac stimulation device for stimulating a heart by varying the pacing interval in a closed-loop control manner responsive to a QT interval in the electrogram signal in order to maintain a normal QT interval.

While the present invention could be implemented in a pacemaker for monitoring and alerting functions and preventative pacing, it is ideally suited for an ICD since backup defibrillation provides an extra level of confidence in terminating a ventricular arrhythmia, should it occur.

BRIEF DESCRIPTION OF THE DRAWINGS

Further features and advantages of the present invention may be more readily understood by reference to the following description taken in conjunction with the accompanying drawings, in which.

DETAILED DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of an Implantable Stimulation Device

Figure 1:
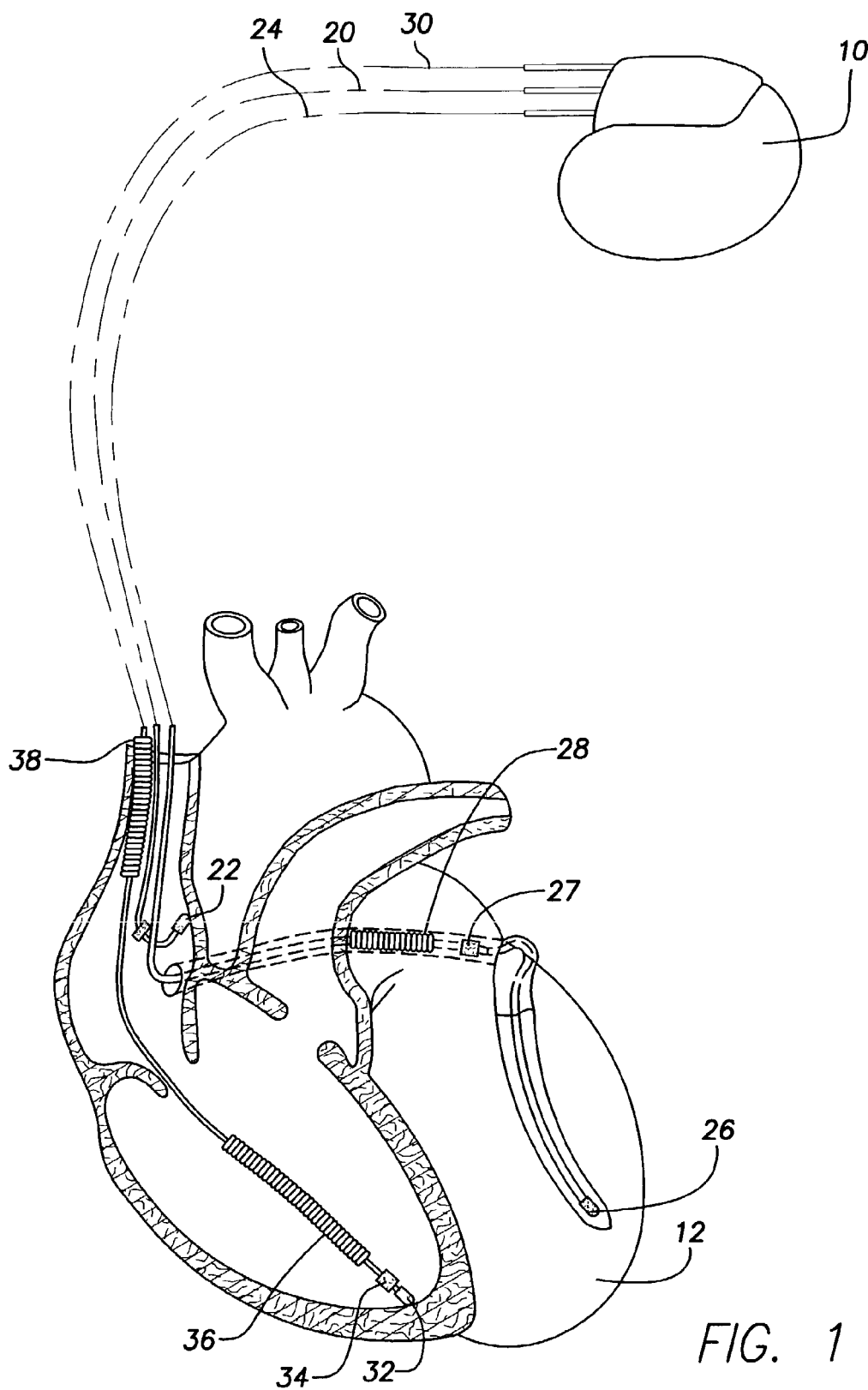
FIG. 1 is a simplified diagram illustrating an implantable stimulation device embodying the present invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVG coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVG coil electrode 38 will be positioned in the superior vena cava.

Accordingly, the right ventricular lead 30 is capable of receiving cardiac signals, and delivering stimulation in the form of pacing and shock therapy to the right ventricle.

Figure 2:
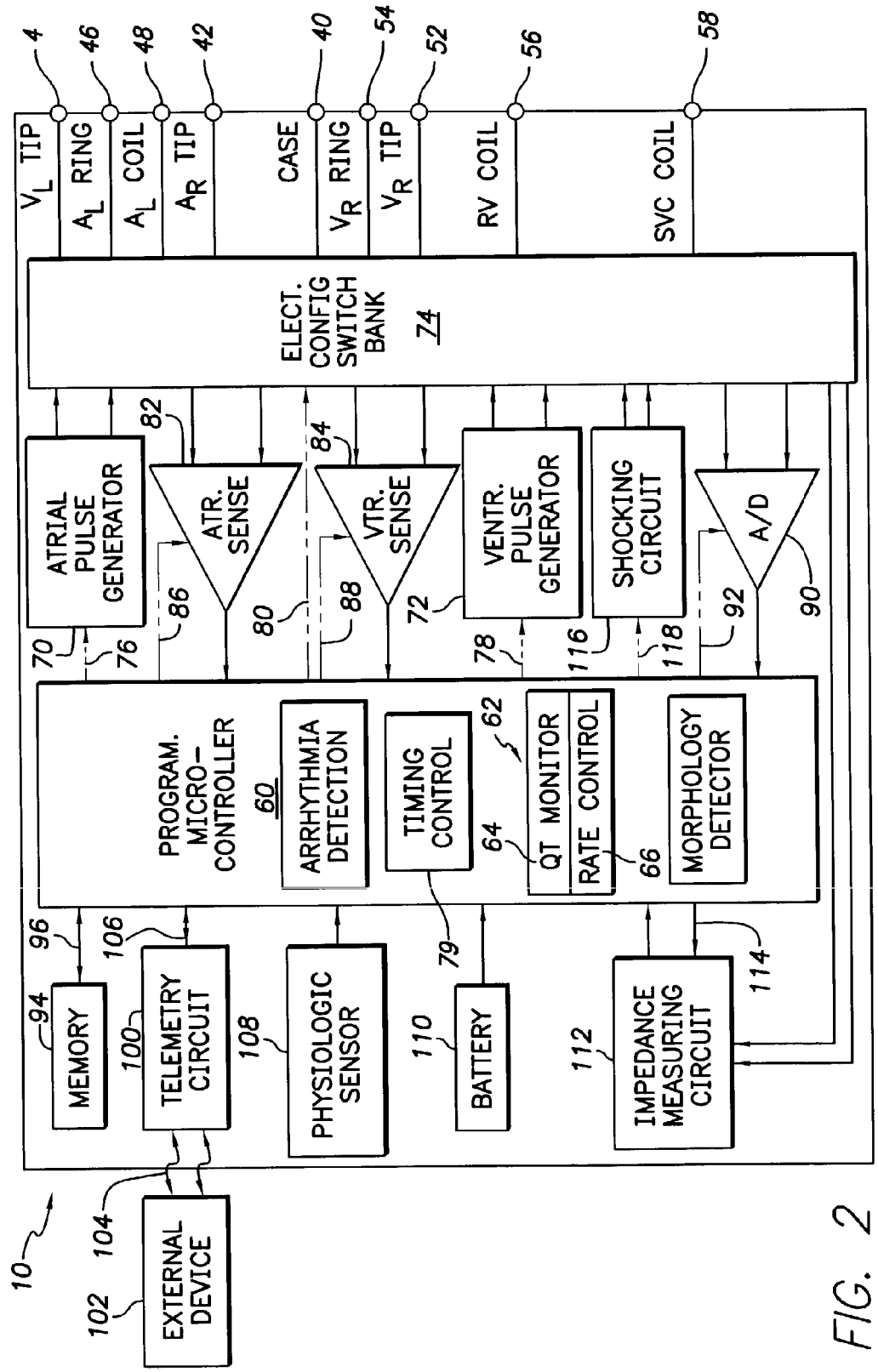
FIG. 2 is a functional block diagram of the implantable stimulation device of FIG. 1 illustrating the basic elements thereof to provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ Coil) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal (RV Coil) 56, and an SVC shocking terminal (SVC Coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and 110 circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate 1/0 circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, band pass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (AID) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 with in each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiologic sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, $V_R$–$V_L$ Delay, etc.) at which the atrial and ventricular pulse generators, 70 and 72, generate stimulation pulses.

The stimulation device additionally includes a battery 110, which provides operating power to all of the circuits shown in FIG. 2. For a stimulation device which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

QT Monitoring and Rate Control

Now that the device 10 has been generally described, additional elements and functions within the device as they more particularly pertain to this embodiment of the present invention will now be described.

In the present invention, the physiologic sensor 108 can be processed to determine daytime and nighttime activity states. For example, in U.S. Pat. No. 5,476,483, Bornzin et. al disclose how to monitor the variance of a physiological sensor, such as a body motion sensor, to determine a threshold of body motion variance. Since body motion varies less during sleep, below a predetermined threshold, the device assumes that the patient is asleep, and above the a predetermined threshold the device assumes that the patient is awake. Accordingly, U.S. Pat. No. 5,476,483 is hereby incorporated herein by reference.

While this technique on detecting sleep and awake states using variance is very highly suitable to body motion, other sensors are may also be used to detect diurnal state. For example, minute ventilation, ventricular gradient (or paced depolarization integral), oxygen saturation, pH, blood flow, cardiac output, sinus rate, and temperature all vary diurnally and may be used directly, or using the variance of these signals, to detect the diurnal state of the patient. It should be noted that the QT interval, while varying diurnally, also exhibits pathologically abnormal variations and therefore is not considered a "true" diurnally varying physiological sensor for purposes of monitoring Long QT Intervals because it cannot be relied upon.

As previously noted, the invention provides a pacing therapy to prevent abnormally long QT intervals which are associated with LQTS, TdP or a ventricular tachyarrhythmia, such as ventricular fibrillation and sudden cardiac death. To that end, the microcontroller further includes a QT module 62 that includes a QT monitor 64 and a QT-dependent rate control 66.

The QT monitor 64, for each cardiac cycle, measures a QT interval (QTI) from one or more electrogram signals sensed by the device 10. The electrogram signal or signals employed may be sensed by the sensing circuits within the data acquisition system 90.

Figure 3:
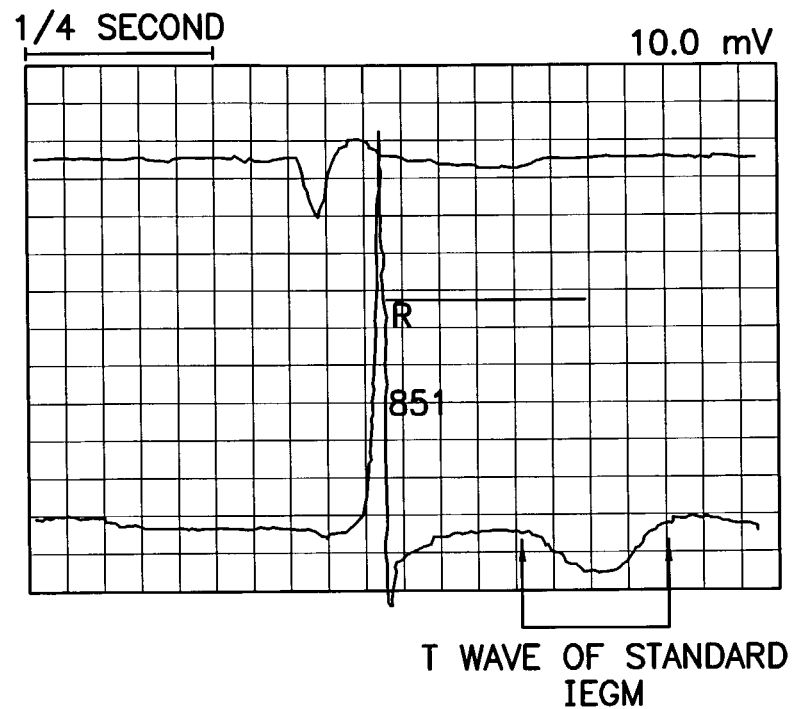
FIG. 3 illustrates an electrogram signal provided by a broad bandwidth sensing circuit.
Figure 4:
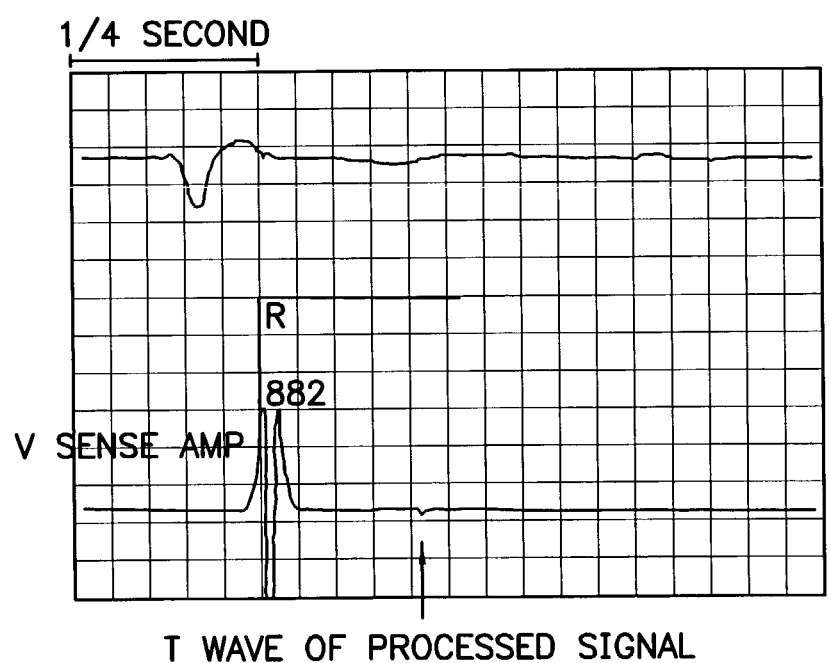
FIG. 4 illustrates an electrogram signal provided by a narrow bandwidth sensing circuit.

Preferably, the sensing circuits for providing the electrogram or electrograms are dedicated sensing circuits having a frequency response low enough to sense and amplify the T-waves of the heart electrical activity from which the pacing therapy may be controlled. FIGS. 3 and 4 illustrate the sensing of a T-wave with, for example, the broad bandwidth of a conventional EGM data acquisition system (such as data acquisition system 90) and the narrow bandwidth of a conventional sensing circuit (such as amplifiers 82 and 84) used to simply control the timing of stimulation pulses, respectively. Note that the narrow bandwidth (shown in FIG. 4) of the standard sense amplifier 84 virtually eliminates the T-wave. Accordingly, such sense amplifiers are not suitable, whereas the broad bandwidth (shown in FIG. 3) of the IEGM data acquisition system 90 is suitable. Alternately, a dedicated independent amplifier may be designed by one of skill in the art.

Figure 5:
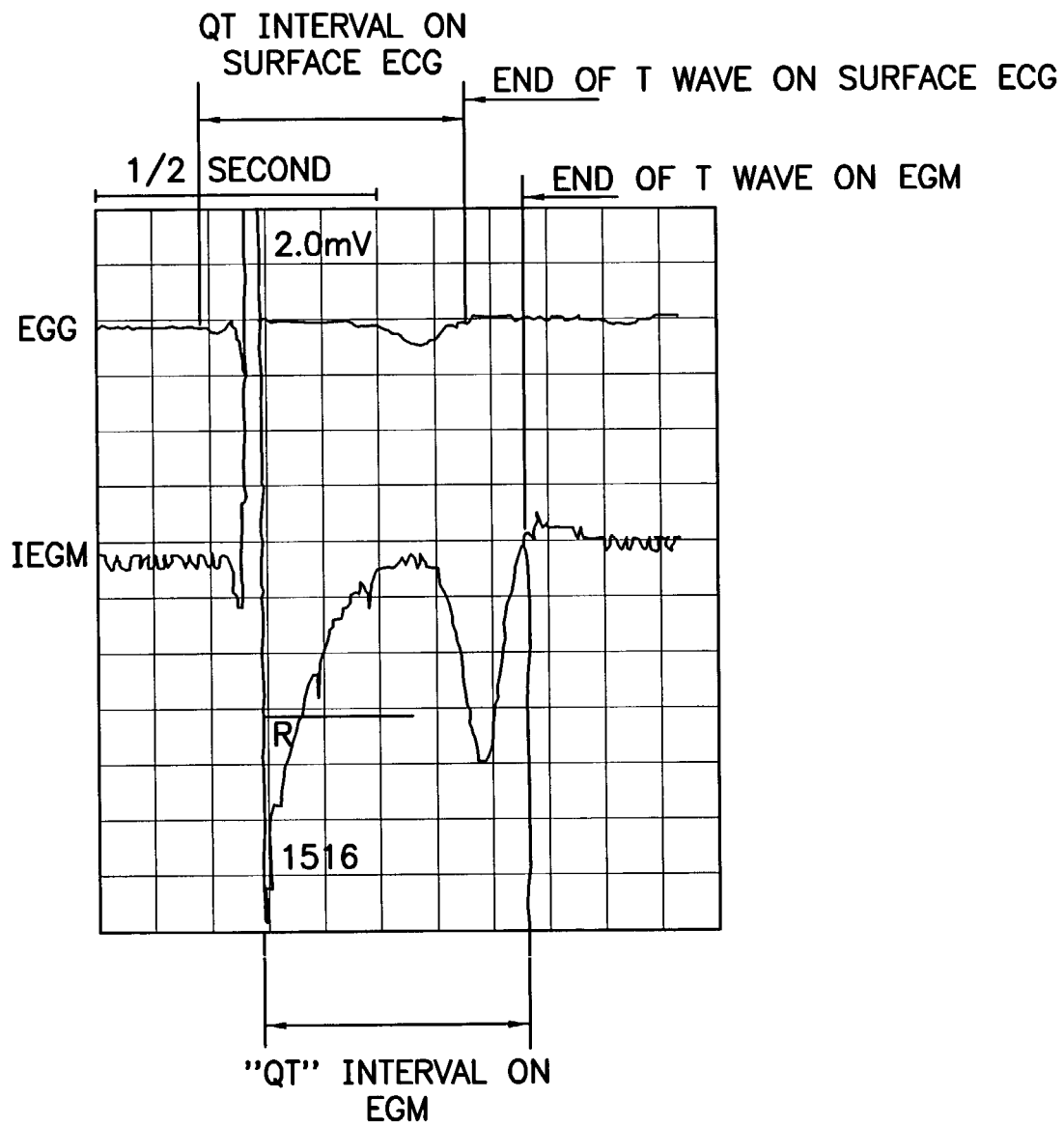
FIG. 5 shows a surface electrocardiogram (ECG) and a corresponding intracardiac electrogram (IEGM) to illustrate respective differences in measuring the QT interval.

FIG. 5 further illustrates measurement differences between the QT interval on a surface electrocardiogram (ECG) and the QT interval on an intracardiac electrogram (IEGM). Accordingly, physicians who are familiar with an expected normal range for QT interval as measured on an ECG will have to be trained to expect a different normal range when viewing the QT interval on an IEGM. Alternatively, other indexing points may be used, such as the peak of the T-wave, to correlate more closely to the end of the T-wave on a surface ECG. Ultimately, it does not matter which index point is used since it is the relative change in the QT interval that is important.

The measured QT interval may be, for example, the QT interval of one or both of the ventricles. As QT intervals exist only for intrinsic heart activity, the QT interval may further be the stim-T interval of one or both ventricles. This will cover timing from initial depolarization through repolarization in both intrinsic and paced cardiac cycles. The analysis of both ventricles may require two separate electrograms to be generated, one for the right ventricle and one for the left ventricle.

Figure 13:
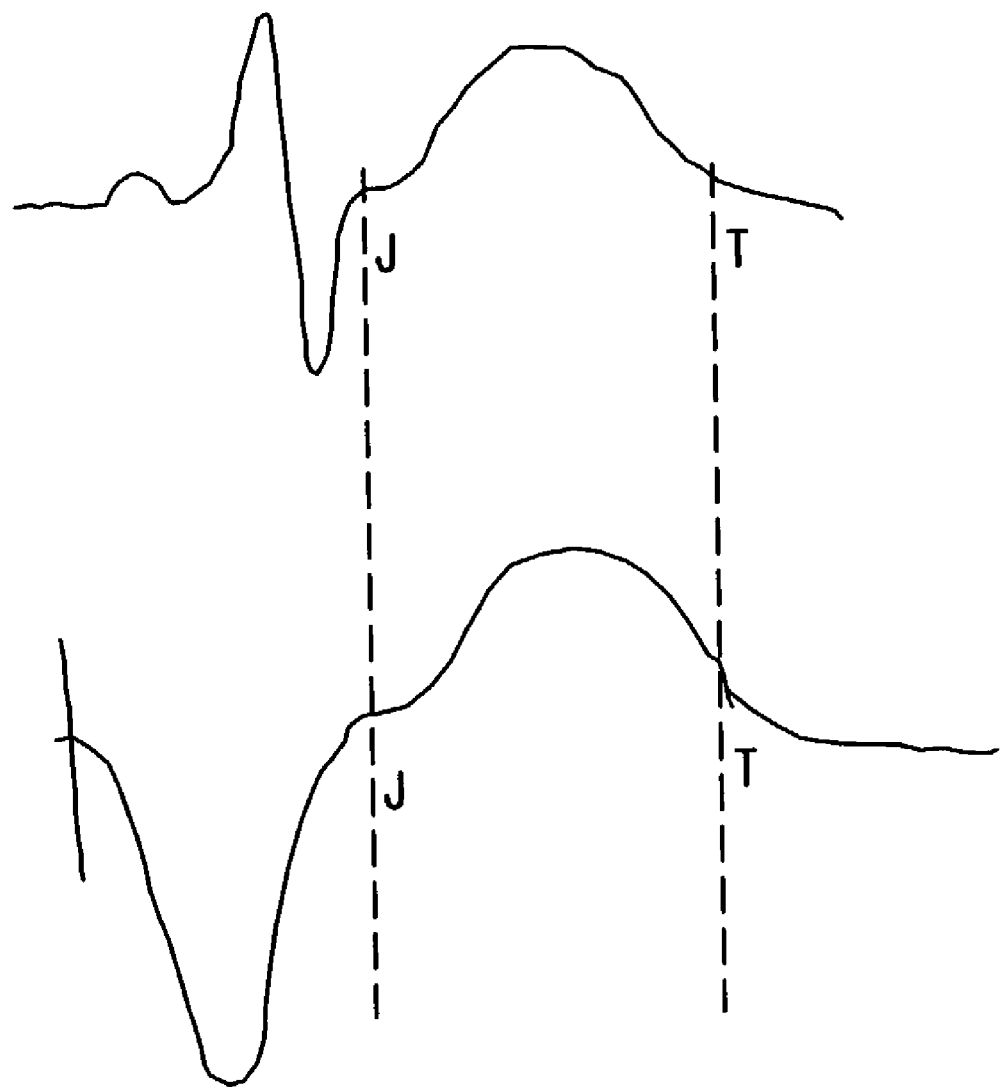
FIG. 13 is an illustration of another technique to measure the QT interval by measuring the J-T interval, which is relatively independent of the type of depolarization (i.e., native or evoked).

Alternatively, the QT interval may actually be the J-T interval, as shown in FIG. 13, which is relatively independent of the type of depolarization (i.e., native or evoked). In this embodiment, the QT interval may be the difference between a J-T interval of one of the ventricles of the heart. In another embodiment, the QT interval may be the difference between a J-T interval of one of the ventricles of the heart and a corresponding J-T interval of the other one of the ventricles of the heart.

In U.S. Pat. No. 4,228,803, Rickards introduced a rate responsive sensor that determined the pacing rate based on a "QT interval". In actuality, this system required a paced ventricular beat and measures an interval from the ventricular pacing stimulus to the apex of the T-wave. Hence, it is more accurately described as a "Stimulus-T (or Stim-T) wave interval". It was observed that the sensing of a shortened Stim-T-wave in the presence of bradycardia indicated the need to increase the pacing rate due to exercise, while the sensing of a longer Stim-T interval corresponded to the need for a desired lower rate, i.e., the pacing interval is adjusted in the same direction as the Stim-T interval, but not necessarily proportional.

The QT interval was found to be a dynamic interval sensitive to circulating catecholamines and exercise stress. This is true for both normal individuals and patients with the LQTS. That is, the QT interval may vary with rate, time of day, physical activity, rest, etc. However, patients who have the LQTS do not have a symptomatic bradycardia to warrant pacing to correct the bradycardia. If not for the repolarization abnormality, they Would not require pacing at all. Thus, a QT or Stim-T rate responsive pacemaker would attempt to decrease the pacing rate in the presence of an abnormally long QT interval, which would further exasperate the long QT interval.

Since the QT interval is subject to diurnal, metabolic, drug, and pathological variations, the invention discriminates between abnormally long QT intervals and physiological variations using the physiologic sensor 108 to detect normal diurnal states of the patient. Contrary to prior rate responsive systems that would decrease the rate in the presence of a long Stim-T interval, when LQTS is detected, the implantable stimulation device of the present invention would increase the stimulation rate so as to shorten the QT interval into a normal range.

Thus, in accordance with the present invention, when the QT interval exceeds a predetermined value corresponding to an abnormally long QT interval condition, the rate control 66 will cause an increase in the pacing rate to override the intrinsic rate, and then to increase the rate only in so far as to maintain the QT interval in a normal range, and only for as long as it is needed.

The rate increase may be gradual over a number of cardiac cycles, which will cause the QT intervals of the heart to shorten. Gradual increment allows the device to make accurate assessments of exactly how much of a rate increase is truly needed. Once the QT interval falls below the predetermined threshold value, the rate control 66 preferably can maintain the rate constant for a predetermined (e.g., programmable) period of time to aid in remodeling of the heart. Alternately, the QT interval may be instantly monitored so as to determine if the heart rate should be decreased on a beat-by-beat basis.

The predetermined threshold value employed by the rate control 66 may be preset (e.g., programmable). For example, the predetermined threshold value may be, 125% to 150% of an expected normal QT interval for the particular patient. This method of programming the threshold value is useful in instances where the patient is chronically in LQTS.

Alternatively, and when the patient is not continuously in LQTS, the predetermined threshold may be learned by the device (e.g., for an activity state). In this instance, the QT monitor 64 may monitor the QT interval over various diurnal states (e.g., corresponding to at least the sleep and awake states) and then compute an average for each state. From the computed average, the predetermined threshold value may then be determined and automatically set by the device. When determining the awake QT Threshold, the device may also exclude QT Intervals during exercise simply by monitoring when the physiologic sensor 108 indicates an exercise state.

Another function of the QT monitor 64 is to provide diagnostic data associated with the QT interval monitoring. The diagnostic data is preferably stored in the memory 94 for later retrieval and transmission to the external receiver 102 by the telemetry circuit 100. The diagnostic data preferably includes a histogram containing a QT interval histogram and a stim-T interval histogram. The histograms may be ultimately displayed in a variety of formats by the programmer (e.g., in bar form, tabular form, or both).

The diagnostic data may also includes an event record. For this purpose, the memory 94 may include a memory portion forming a FIFO memory wherein pacing state and pacing rate data may be stored over a last time period of, for example, 24 hours. The pacing state data may include pacing mode and the number of paced beats. The event record may also include a plot of QT interval versus time. Again, the plotted data may be for data generated during a last time period of, for example, 24 hours. The histograms may be updated with each cardiac cycle. However, the event record and plotted data may be updated less frequently. For example, the event record and plotted data may be updated every 30 seconds, for example.

Since it is believed a prolongation of the inter-ventricular delay (V—V delay) may contribute to the widening of the QT interval (i.e., that the increase in the V—V delay is manifested on a surface ECG as the vector sum of the lengthening of the repolarization waveforms of each ventricle as they superimpose out of synchronization), it is contemplated that the implantable device could monitor any changes in the V—V timing.

Accordingly, the diagnostic data may include changes in the $V_{Right}$–$V_{Left}$ Delay (i.e., detecting a sudden increase or a gradual progression up to a predetermined threshold). In another embodiment, the diagnostic data may include the sequence of activation and a change in the sequence of activation (i.e., a change in direction from $V_{Right}$–$V_{Left}$ to $V_{Left}$–$V_{Right}$). In another embodiment, the diagnostic data may include the Right QT Interval and the Left QT interval or a comparison thereof. In another embodiment, the diagnostic data may include the amplitude of the Left T-wave compared to the Right T-wave (i.e., corresponding to the presence of T-wave alternans).

Measurements for the QT interval could be performed periodically: less frequently during periods of sleep (for an accurate, and/or non-stressed baseline); more frequently during known periods of higher incidence of SCD, such as the pre-dawn hours; at periodic intervals during the day corresponding to the awake state (as detected by activity variance) with an appropriate frequency to track drug changes; exclude periods of exercise; and/or manually by the patient. The device could also time stamp such changes for determining whether they correspond to drug dose cycles.

The foregoing provides a therapy for long QT interval conditions to prevent TdP, ventricular fibrillation, syncope and/or sudden cardiac death that may otherwise result from long QT intervals. The increased pacing rate serves to shorten the QT interval to provide the above-noted prevention therapy. However, the increased pacing rate is provided only when necessary and thus avoids the problems which may result from chronic high rate heart activity.

In addition to providing the preventive therapy, the present invention provides important diagnostic data for use by the physician. The diagnostic data which directly relates to LQTS and will assist the physician in titrating treatment.

Before more particularly describing the embodiments of FIGS. 6–12, it may also be helpful to describe the types of pacing, which may be employed in accordance with the present invention. Firstly, single chamber ventricular pacing may be utilized. This form of pacing may be most beneficial for those patients having uniform QT intervals for both the right and left ventricles. For patients having differing QT intervals in the right and left ventricles, dual chamber pacing, wherein the atrial pacing rate is increased, may be most beneficial. Lastly, bi-ventricular pacing, wherein both the right and left ventricles are paced simultaneously, may be especially helpful for those patients with wide QRS complexes. It has been shown that bi-ventricular pacing can narrow the QRS complex and improve hemodynamics in the heart.

Figure 6:
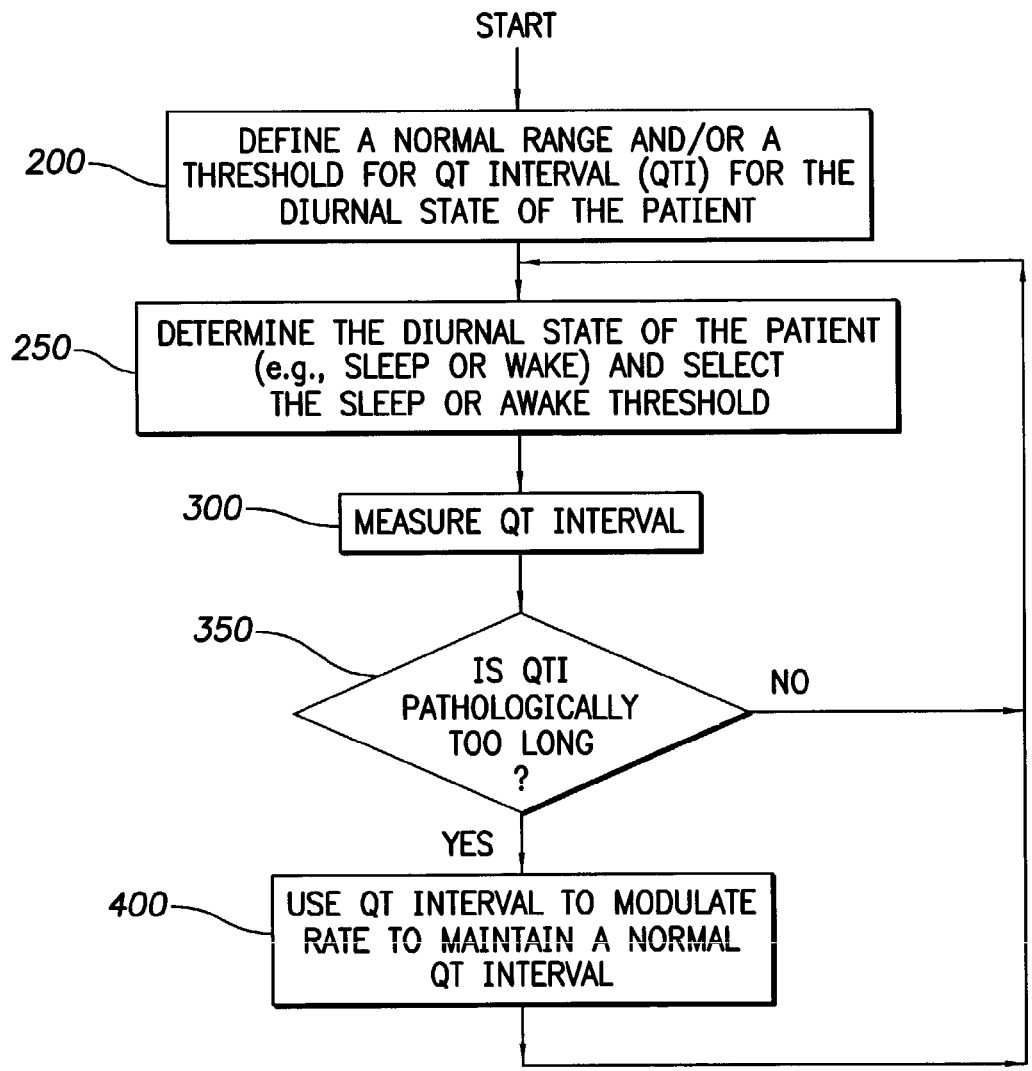
FIG. 6 is a flow chart describing a general overview of the operation of one embodiment of the present invention for treating abnormal ventricular activation-recovery time.

In FIG. 6, a flow chart is shown describing an overview of the operation and novel features implemented in one embodiment of the device 10. In this flow chart, and the flow charts of FIG. 7-12 described herein, the various algorithmic steps are summarized in individual "blocks". Such blocks describe specific actions or decisions that must be made or carried out as the algorithm proceeds. Where a microcontroller, or equivalent, is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

In FIG. 6 is a flow chart describing a general overview of the operation of one embodiment of the present invention for treating abnormal ventricular activation-recovery time. As shown in FIG. 6, the process starts by defining a normal range and/or a QT Interval (QTI) for the diurnal state of the patient, at step 250. It is contemplated that at implant, the predetermined threshold value employed by the rate control 66 would be preset (e.g., programmable), as describe above, using for example, 125% to 150% of an expected normal QT interval for the particular patient. As will be shown in conjunction with FIGS. 7 and 8, the device may also learn an appropriate QT Interval for various diurnal states (e.g., at least day and night).

Next, at step 250, the process will determine the diurnal state of the patient based on the physiologic sensor 108.

At step 300, the QT monitor 64 then measures the QT Interval for that diurnal state. The microcontroller 60 then sets the QT Threshold as either the daytime threshold, QT Awake, or the nighttime threshold, QT Sleep. Step 250 is described in more detail in conjunction with FIGS. 7 and 8.

At step 350, the microcontroller 60 then determines if the QT Interval is pathologically too long. If it is not, the process then loops back to step 250 and continues to monitor the diurnal state and the QT Interval. If the QT Interval is pathologically too long, then the QT Interval is monitored in step 400 while adjusting the pacing rate to find an appropriate rate that sufficiently causes the QT Interval to shorten to a normal range, thereby altering the refractoriness of the cardiac tissue. Steps 350 and 40 are described in more detail in conjunction with FIGS. 9 and 10.

Figure 7:
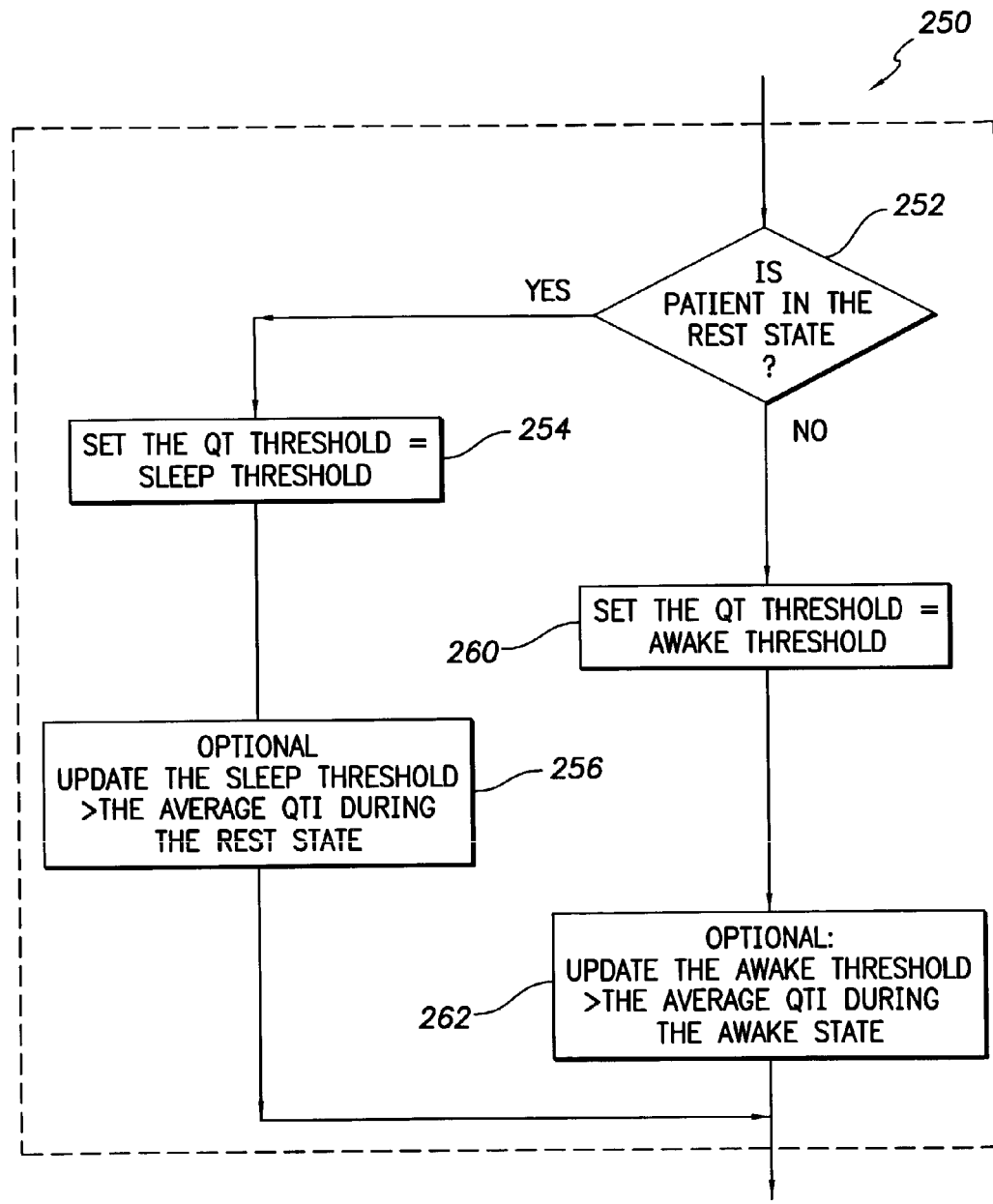
FIG. 7 is a flow chart describing the subroutine 250 of FIG. 6 for determining the diurnal state of the patient and, optionally, learning the QT interval thresholds for the various diurnal states.

FIG. 7 is a flow chart describing the subroutine 250 of FIG. 6 for determining the diurnal state of the patient and, optionally, learning the QT interval thresholds for the various diurnal states.

Figure 8:
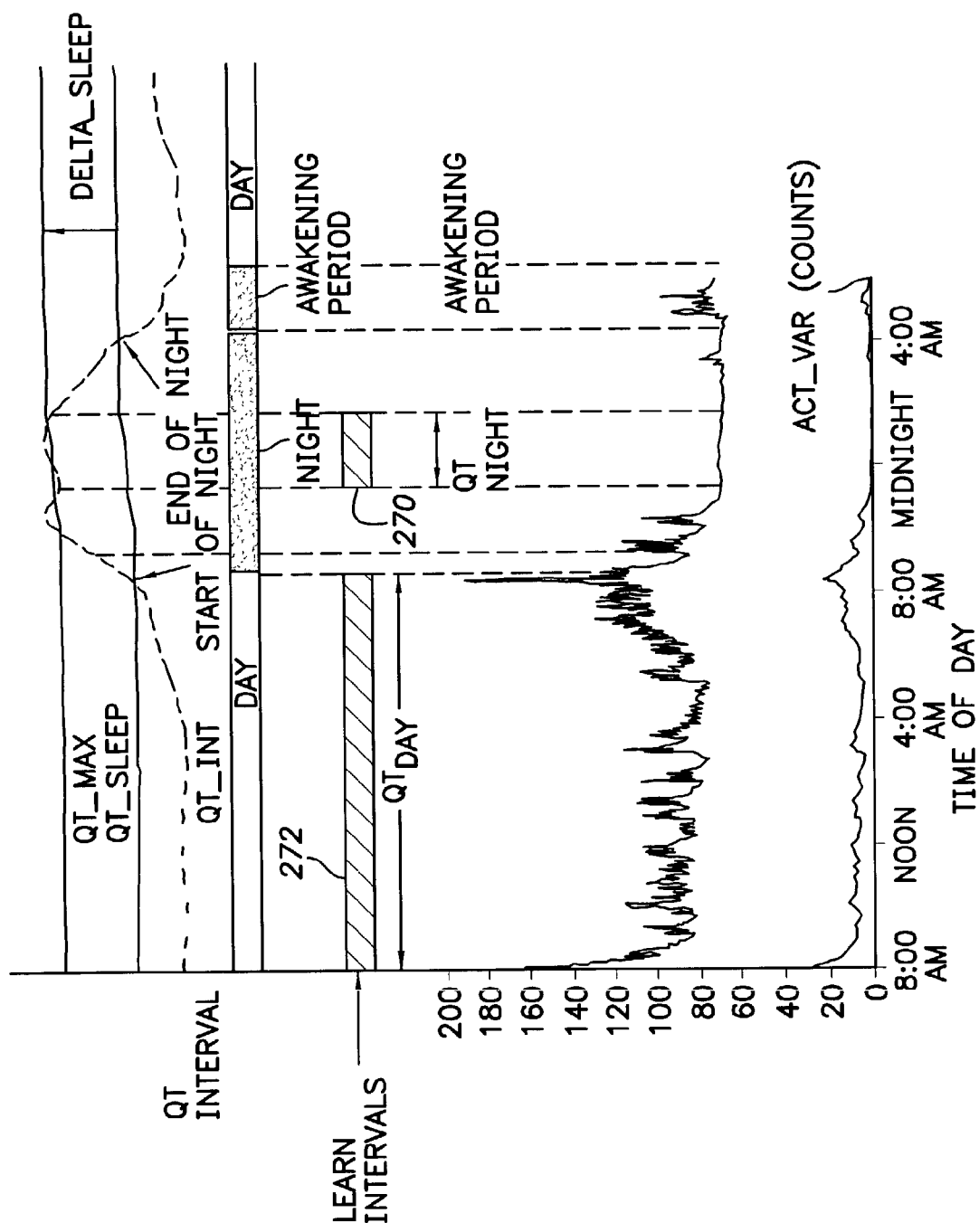
FIG. 8 is a graph of the activity states, as determined by the diurnal sensor, versus the diurnal QT Interval signal.

FIG. 8 is a graph of the activity states as determined by, for example, the variance of a body motion sensor, versus the diurnal QT Interval signal. As illustrated in FIG. 8, the rest state is determined by measuring the physiologic sensor 108 (in this instance, the sensor shown is body motion) to determine the variance thereof, and thereby detecting a marked decrease during sleep. While the QT Interval shown is one of a healthy-QT patient, it is also known that there is a higher incidence of tachyarrhythmias in the early morning hours which may be due to the inability of the patient's heart to resume a normal QT interval upon wakening. Accordingly, the physiologic sensor 108 may be used to begin shortening of the QT interval in the awakening period.

As shown in FIG. 7, the microcontroller 60 determines if the patient is in the rest state, in step 252. If the patient is in the rest state for a prolonged period of time, the microcontroller presumes that it is nighttime and sets the QT threshold to a Sleep Threshold. During a period such as $QT_{Night}$ (at 270 of FIG. 8), the QT monitor 64 can (optionally) monitor the QT Interval and store these values in memory 94. The microcontroller 60 subsequently averages these values to learn a more accurate nighttime value for QT interval for the particular patient.

If the patient is not in the rest state, as detected by the physiologic sensor 108, then the process will microcontroller presumes that it is daytime and sets the QT threshold to an Awake Threshold. During a period such as $QT_{Day}$ (at 272 of FIG. 8), the QT monitor 64 can again monitor the QT Interval and store these values in memory 94. The microcontroller 60 subsequently averages these values to learn a more accurate daytime value for QT interval for the particular patient.

Figure 9:
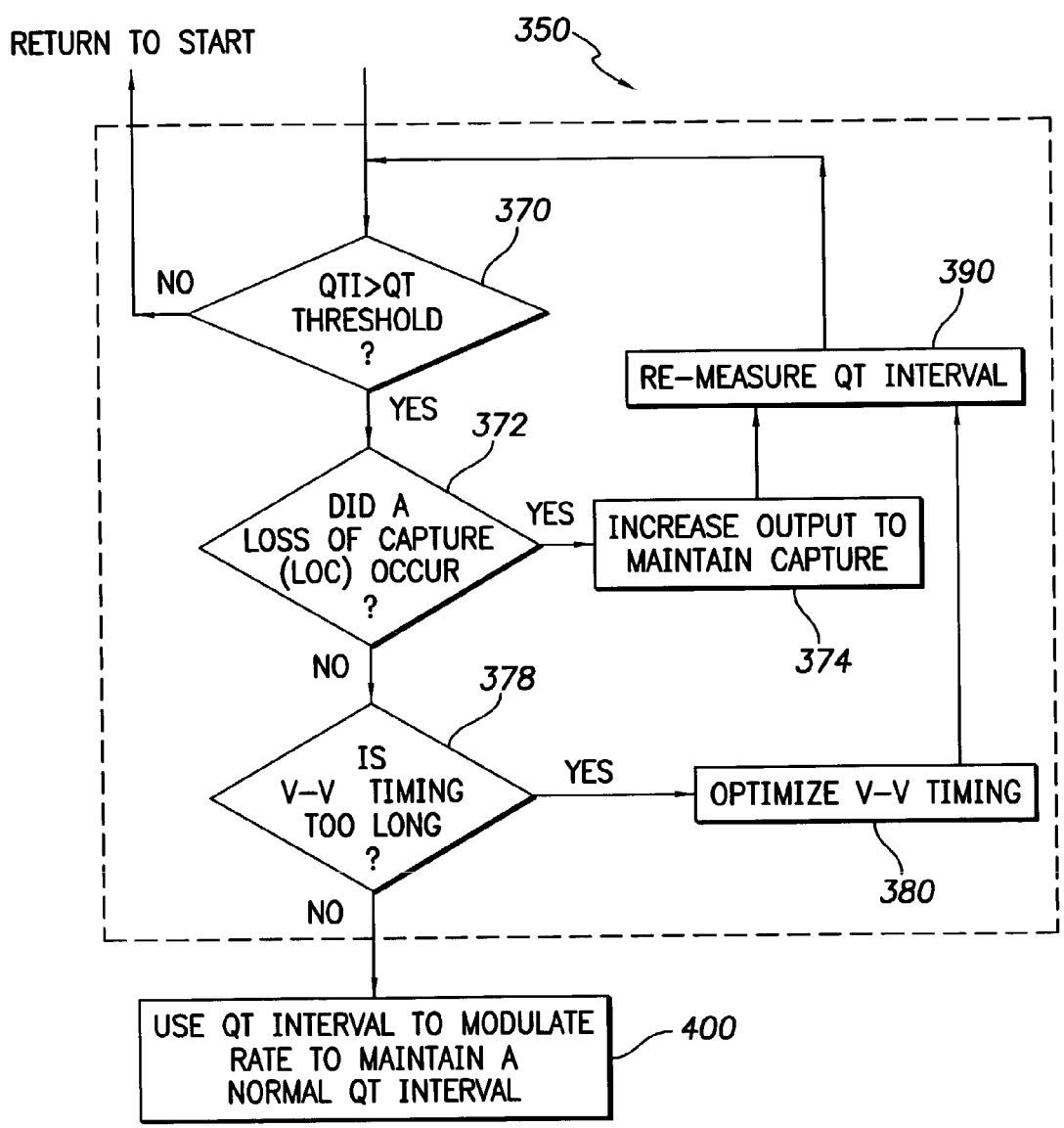
FIG. 9 is a flow chart describing the subroutine 350 of FIG. 6 for detecting abnormally long QT intervals and discriminating against false positives due to loss of capture and/or inappropriate V—V timing intervals.

FIG. 9 is a flow chart describing the subroutine 350 of FIG. 6 for detecting abnormally long QT intervals and discriminating against false positives due to loss of capture and/or inappropriate V—V timing intervals. Once the QT Interval has been measured (in step 300 of FIG. 6), the process compares the measured QT Interval to see if it is greater than the QT Threshold. As determined in the preceding subroutine of FIG. 7, the microcontroller already has detected the patient's diurnal state, and chosen the QT Threshold to be either the daytime, Awake Threshold, or the nighttime, Sleep Threshold, value. If the QT Interval does not exceed the current QT Threshold, the process returns to the Start.

If the current QT Threshold is exceeded, then a determination is made at step 372 to verify that the long QT interval is not due to a loss of capture in either chamber. Loss of capture typically will cause the QRS width to widen, which may falsely indicate a sudden lengthening of the QT interval. If loss of capture has occurred, the output is increased according to an automatic capture routine until capture is found (in step 374). For a complete description of a suitable automatic capture technique, see for example, U.S. patent application Ser. No. 10/124,164 or U.S. Pat. No. 5,697,956.

The process continues to step 390 wherein the QT Interval is re-measured and then compares the measured QT Interval to the QT Threshold in step 370

If the QT Interval is still long, and both chambers are capturing (step 372), then the process examines the V—V timing interval to see if it needs to be adjusted. If so, then the process proceeds to step 380, wherein the V—V timing is adjusted through several values to see if it improves the QT Interval (step 380) and continues to re-measure the QT Interval (step 390) and compares it to the QT Threshold (step 370). If the V—V timing cannot be optimized further, and the QT Interval is still long, then the system will begin to modulate the pacing rate to shorten the QT Interval (step 400).

While the steps of detecting loss of capture (372, 374) and optimizing the V—V timing (378, 380) aid in preventing false positive detections, their location in the subroutine shown in FIG. 9 is still optional, as these steps may be placed elsewhere in the pacing therapy, and is shown here for completeness for determining that the QT Interval is pathologically long, and not due to these other conditions. In fact, these steps (372, 374, 378, 380) are preferably done before step 200 in FIG. 6 so that therapy can be delivered promptly.

Figure 10:
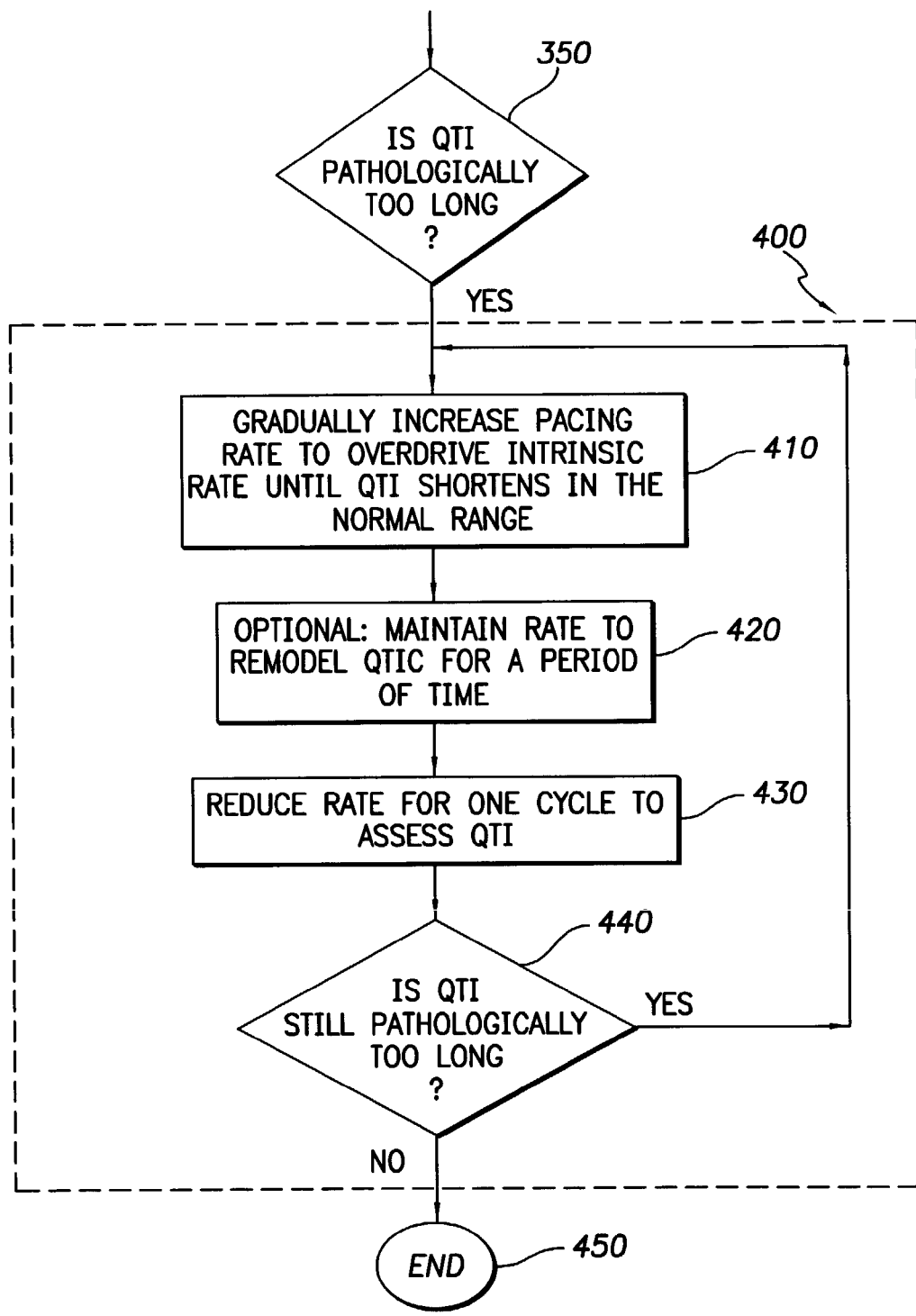
FIG. 10 is a flow chart describing the subroutine of FIG. 6 for adjusting the rate to maintain a normal QT interval.

FIG. 10 shows a flow chart describing the subroutine 400 of FIG. 6 for adjusting the rate to maintain a normal QT interval. As shown in FIG. 10, once the QT Interval is determined to be pathologically too long, the process advanced to step 410 wherein the pacing rate is gradually increased to overdrive the intrinsic rate and stops increasing the rate when the QT Interval shortens to a normal range, e.g., below the current QT Threshold for that diurnal state.

In step 420, the process may, optionally, maintain the rate for a period of time to enhance and encourage the heart to remodel back to a healthy substrate. After the period of time has expired (or when this option is not selected), the system will lower the rate for one cycle (step 430) and continuously monitor to determine if the QT Interval is pathologically too long in step 440, which are identical to the subroutine 250 (i.e., check diurnal state of the patient and used the appropriate QT Threshold). If so, the process loops back to step 410 wherein the rate will again increase to maintain the QT Interval within a normal range. When the QT Interval starts to naturally shorten (e.g., due to remodeling or other physiological conditions), then the rate will gradually be reduced in so far as to maintain a normal QT Interval, and when no longer long, the process will end in step 450.

Figure 11:
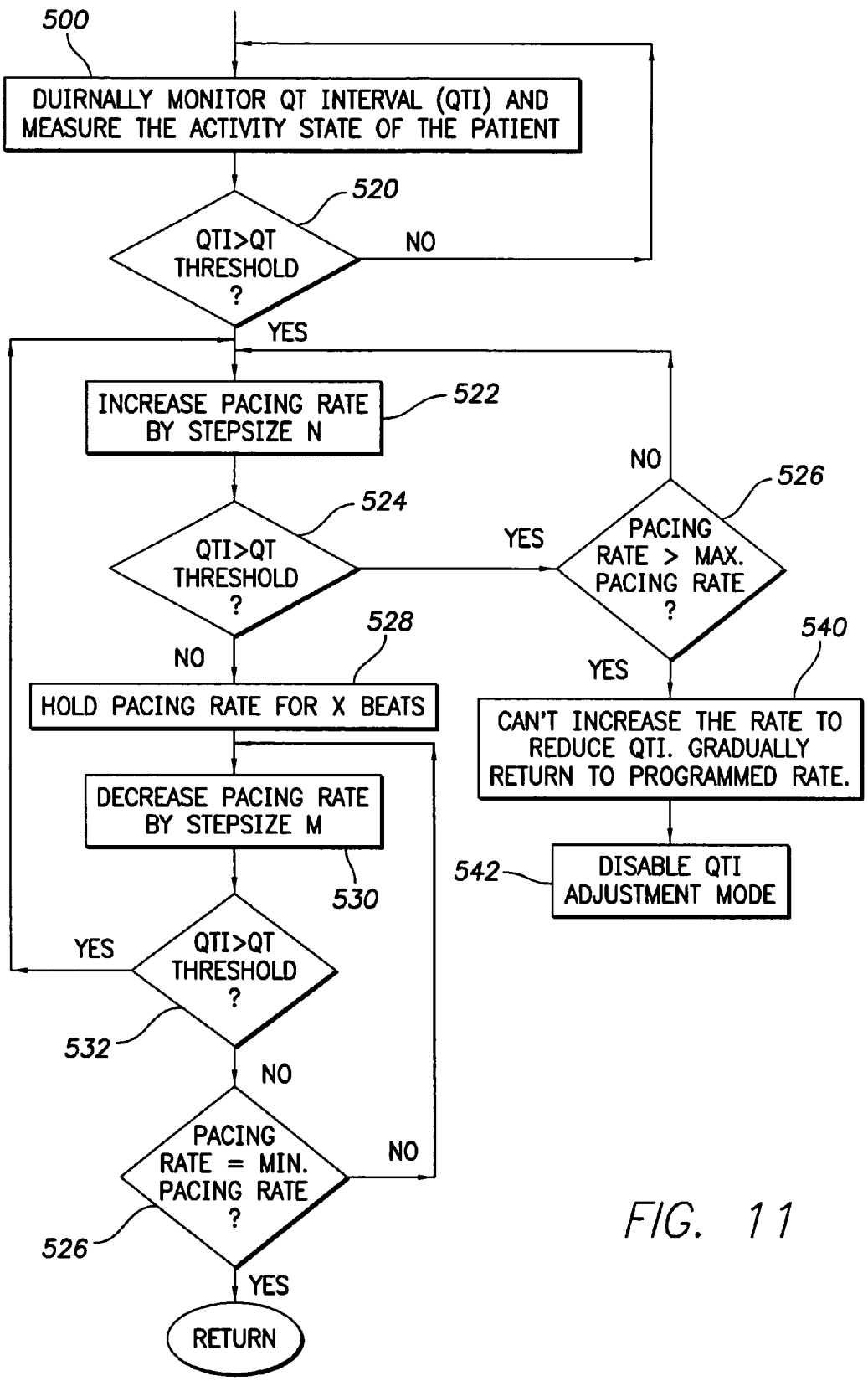
FIG. 11 is a flow chart describing a more detailed description of another embodiment of the present invention for providing closed loop control.

FIG. 11 is a flow chart describing a second embodiment, which provides a more detailed description for providing closed loop control. As illustrated in FIG. 11, the process illustrated initiates with a subroutine 500. In subroutine 500, the QT interval is monitored diurnally (e.g., continuously over 24 hour periods) (as described, for example, in FIG. 12), and the activity state of the patient is also determined, as previously described in FIG. 7.

Next, in decision block 520, the rate control 66 determines if the QT interval is greater than the predetermined QT Threshold, which may be learned or preset. As described above, the QT Threshold will be an Awake QT value when the patient is detected to be awake, and a Sleep QT Threshold value when the patient is detected to be asleep.

If the QT interval is not greater than the predetermined QT Threshold, the process returns to the subroutine 500. However, if the QT interval is greater than the predetermined QT Threshold, the process then advances to activity block 522 wherein the pacing rate is increased, for example, by a step of size "N".

As previously mentioned, the pacing may be single chamber ventricular pacing, dual chamber pacing, or bi-ventricular pacing.

After the pacing rate has been increased, the process advances to decision block 524 where it is once again determined by the rate control 66 if the QT interval is greater than the predetermined QT Threshold. If the QT interval is still greater than the QT Threshold, the process advances to decision block 526 wherein the rate control 66 determines if the current rate is greater than a predetermined maximum pacing rate. If the current rate is not greater than a predetermined maximum pacing rate, the process then returns to activity block 522 for the next increase in the pacing rate. However, if the current pacing rate is equal to or greater than the predetermined maximum pacing rate, the process then advances to activity block 540 wherein the pacing rate is decreased to a normal rate and the therapy is aborted in step 542.

If in decision block 524 it is determined that the QT interval has fallen below the QT Threshold due to the increase in pacing rate in step 522, then the process advances to activity block 528 wherein the current pacing rate may be optionally held for a preset period of time at an "intervention rate". This maintaining of the intervention rate is to encourage remodeling, and may be a programmable value. Once the pacing rate has been held for the desired amount of time (or zero), the process then advances to activity block 530, wherein the rate is decreased one step at a time, in predetermined increments of size "M".

In accordance with one embodiment, the decrease in pacing rate may be made in accordance with a recovery mode, such as a fallback mode or rate smoothing mode, which eventually restores the heart rate to a normal physiologically mandated rate. When the pacing rate is returned to the normal rate, the process then returns.

In a preferred embodiment, the pacing rate is decreased and monitored in block 532 for a corresponding lengthening of the QT Interval until an appropriate level is maintained. As soon as the QT Interval exceeds the QT threshold, the process will loop back to step 522 and the rate will increase. This is the basis (and one technique for implementation) for closed-loop control.

Figure 12:
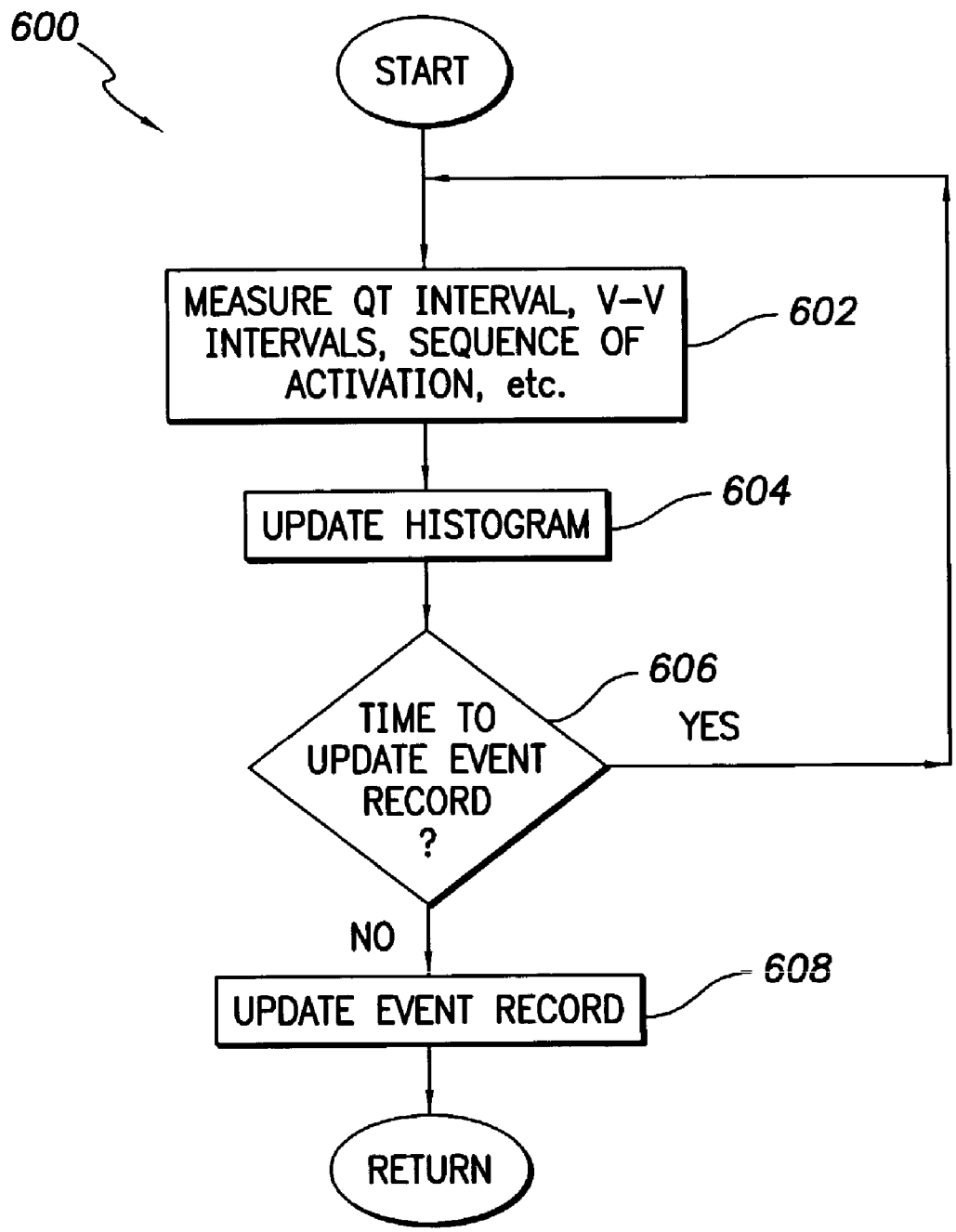
FIG. 12 is a flow chart describing the subroutine of FIG. 11 for monitoring QT intervals.

Referring now to FIG. 12, a flow diagram is shown more particularly describing a method of diurnally monitoring the QT Interval using histograms that may be used in step 500 of FIG. 11. The subroutine initiates at an activity block 602 where the QT interval is measured.

As previously mentioned, the QT interval may be the QT interval of one of the ventricles, the stim-T interval of one of the ventricles, or a difference between the QT or stim-T interval of one ventricle and the corresponding QT or stim-T interval of the other ventricle.

As described above, the diagnostic data may include changes in the $V_{Right}$–$V_{Left}$ Delay (i.e., detecting a sudden increase or a gradual progression up to a predetermined threshold); the sequence of activation; a change in the sequence of activation (i.e., a change in direction from $V_{Right}$–$V_{Left}$ to $V_{Left}$–$V_{Right}$); a respective Right QT Interval and the Left QT Interval; a comparison of the Right QT and Left QT Intervals; the amplitude of the Left T-wave compared to the Right T-wave (i.e., corresponding to the presence of T-wave alternans), or other indicator of dyssynchrony between the left and right chambers.

When the QT interval has been measured in accordance with activity block 602, the process then advances to activity block 604 to update the histogram, which has been previously described. Once the histogram has been updated, the process advances to decision block 606 to determine if it is time to update the event record. As previously mentioned, the event record need not be updated as frequently as the histogram and, may be updated, every 30 seconds, for example.

If it is not time to update the event record, the subroutine returns. However, if it is time to update the event record, the process advances to activity block 608 wherein the event record is updated.

As previously mentioned, the QT interval may be a difference between the QT interval or stim-T interval of one ventricle and the corresponding QT interval or stim-T interval of the other ventricle. This QT interval may be employed in practicing the present invention since it has been demonstrated that regional differences can occur in QT interval prolongation in a pharmacologic model for LQTS. Differences in repolarization have been induced during pacing by insertion of premature stimuli. A permanent pacing lead in the right ventricle demonstrated the least variability while the greatest variability in activation-recovery intervals (ARI) which is roughly equivalent to the local QT interval occurred in the left ventricle. As the ARI dispersion increased in the left ventricle, TdP was easier to induce. In addition, the differences in relative dispersion of refractoriness were greatest at the low rates (approximately 60 beats per minute) compared to faster rates. Through the use of plunge electrodes inserted in the myocardium, differences between the endocardium, mid-muscle and epicardial layers could be demonstrated.

Although a similar model may not be feasible for the patient with a permanent pacing system, the relative difference in QT interval between the right ventricular lead and a left ventricular lead to serve as a marker or indicator of impending difficulties may be employed. This would lend itself for use in bi-ventricular pacing systems and, as previously noted, require independent sensing circuits for generating a right ventricular electrogram and a left ventricular electrogram. Hence, as contemplated herein, the activity block 602 could encompass the measurement of a difference in the QT interval or stim-T interval between the right ventricle and the left ventricle. The difference may then be the QT interval, which is compared against a QT Threshold for purposes of controlling pacing rate. If the difference starts to increase, even though the actual QT interval still remains within a normal range, the difference could serve as a marker for developing problems, which could then be managed by increasing the pacing rate as described herein.

As also previously described, when the QT interval is based upon the difference between the QT interval or stim-T interval of the right ventricle and the corresponding QT interval or stim-T interval of the left ventricle, dual chamber pacing may be most beneficial to the patient. With such dual chamber pacing, the increase in pacing rate may be implemented by increasing the atrial-pacing rate. For pacing the ventricles, either one ventricle may be paced or the ventricles may be paced simultaneously or sequentially in a bi-ventricular pacing mode.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device, comprising:
   a physiological sensor that detects a physiologic parameter associated with a diurnal state of the patient;
   a QT measuring circuit that measures a QT interval based on at least one of an evoked cardiac event or an intrinsic cardiac event;
   a pulse generator that delivers pacing pulses to at least one chamber of the patient's heart at an adjustable pacing rate;
   a control circuit connected to the physiological sensor, pulse generator, and to the QT measuring circuit, wherein the control circuit is operative to process the physiological parameter to determine the diurnal state, and that is operative to determine when the measured QT interval is abnormally lone for the diurnal state, and that is operative to adjust the pacing rate to shorten the QT interval to within a normal range;
   wherein the control circuit increases the pacing rate when a measured QT interval exceeds a QT Threshold; and
   a memory circuit for storing a QT sleep threshold and a QT awake threshold; and
   wherein the control circuit uses the stored QT sleep threshold as the QT Threshold when the patient is in a sleep state, and uses the QT awake threshold as the QT Threshold when the patient is in an awake state.

2. The device of claim 1, wherein:
   the control circuit maintains the pacing rate in a normal range in a closed loop manner by adjusting a pacing interval in an opposite direction of the measured QT interval.

3. The device of claim 1, wherein the QT sleep threshold is a programmable value.

4. The device of claim 1, wherein the QT awake threshold is a programmable value.

5. The device of claim 1, wherein:
   the physiologic sensor detects sleep and awake states; and
   the control circuit adjusts the pacing rate to maintain the QT interval below the QT sleep threshold when the patient is detected in the sleep state, and adjusts the pacing rate to maintain the QT interval below the QT awake threshold when the patient is detected in the awake state.

6. The device of claim 1, wherein:
   the control circuit updates the QT sleep threshold and the QT awake threshold based on QT intervals measured during the sleep and wake states, respectively.

7. The device of claim 6, wherein:
   the control circuit updates the QT sleep and QT awake thresholds based on an average of the QT intervals measured during the sleep and wake states, respectively.

8. The device of claim 1, wherein the QT interval is a QT interval of one of the ventricles.

9. The device of claim 1, wherein the QT interval is a stim-T interval of one of the ventricles.

10. The device of claim 1, wherein the QT interval is a J-T interval of one of the ventricles.

11. The device of claim 1, wherein the pulse generator is configured to deliver pacing pulses to one of the ventricles of the heart.

12. The device of claim 1, wherein the pulse generator is configured to deliver pacing pulses to both ventricles of the heart.

13. The device of claim 1, wherein the pulse generator is configured to deliver pacing pulses to an atrium of the heart.

14. The device of claim 1, further comprising;
a memory that stores the diagnostic data; and
wherein the control circuit triggers the storage of measured QT interval diagnostic data into the memory.

15. The device of claim 14, wherein the diagnostic data comprises a histogram data.

16. The device of claim 15, wherein the histogram data comprises at least one of QT interval histogram data, stim-T interval histogram data and J-T interval histogram data.

17. The device of claim 14, wherein the diagnostic data comprises time stamping so that a QT interval may be plotted over time.

18. The device of claim 14, wherein the diagnostic data comprises storing changes in the $V_{Right}-V_{Left}$ Delay.

19. The device of claim 18, wherein the diagnostic data comprises storing a sudden change in the $V_{Right}-V_{Left}$ Delay.

20. The device of claim 18, wherein the diagnostic data comprises storing a gradual change in the $V_{Right}-V_{Left}$ Delay.

21. The device of claim 14, wherein the diagnostic data comprises storing a sequence of activation between the patient's left and right cardiac depolarizations.

22. The device of claim 21, wherein the diagnostic data comprises storing a change in the sequence of activation.

23. The device of claim 14, wherein the diagnostic data comprises storing Right QT Interval and the Left QT interval.

24. The device of claim 14, wherein the diagnostic data comprises storing an amplitude of the Left T-wave compared to the Right T-wave.

25. The device of claim 14, wherein the diagnostic data comprises periodically storing measurements for the QT interval less frequently during periods of sleep.

26. The device of claim 14, wherein the diagnostic data comprises periodically storing measurements for the QT interval more frequently during known periods of higher incidence of SCD.

27. The device of claim 14, wherein the diagnostic data comprises periodically storing measurements for the QT interval more frequently during a brief awakening period which immediately follows the sleep state.

28. The device of claim 14, wherein the diagnostic data comprises periodically storing measurements for the QT interval at periodic intervals during the day corresponding to the awake state with an appropriate frequency to track drug changes.

29. The device of claim 1, wherein the physiologic sensor detects a physiologic parameter of the patient's body that changes during at least sleep and awake states of the patient.

30. The device of claim 29, wherein the physiologic sensor is a body motion sensor.

31. The device of claim 29, wherein the physiologic sensor is a minute ventilation sensor.

32. The device of claim 29, wherein the physiologic sensor is a temperature sensor.

33. The device of claim 29, wherein the physiologic sensor is an oxygen saturation sensor.

34. The device of claim 29, wherein the physiologic sensor is a blood flow sensor.

35. The device of claim 29, wherein the physiologic sensor is a cardiac output sensor.

36. The device of claim 29, wherein the physiologic sensor is a pH sensor.

37. The device of claim 29, wherein the physiologic sensor is a rate detector that detects the patient's sinus rate.

38. The device of claim 29, wherein the physiologic sensor is an electrogram integrator that integrates an evoked response to produce a paced depolarization integral.

39. The device of claim 29, wherein the physiologic sensor is processed to determine the variance of the physiologic parameter of the patient, wherein a low variance indicates a sleep state and a high variance indicates an awake state.

40. An implantable cardiac stimulation device, comprising:
a physiological sensor that detects a physiologic parameter associated with a diurnal state of the patient;
a QT measuring circuit that measures a QT interval based on at least one of an evoked cardiac event or an intrinsic cardiac event;
a pulse generator that delivers pacing Pulses to at least one chamber of the patient's heart at an adjustable pacing rate; and
a control circuit connected to the physiological sensor, pulse generator, and to the QT measuring circuit, wherein the control circuit is operative to process the physiological parameter to determine the diurnal state, and that is operative to determine when the measured QT interval is abnormally long for the diurnal state, and that is operative to adjust the pacing rate to shorten the QT interval to within a normal range;
wherein the control circuit verifies that capture is maintained in at least one ventricle before assessing whether the QT interval is abnormally long.

41. The device of claim 40, wherein:
the control circuit verifies that capture is maintained in both ventricles before assessing whether the QT interval is abnormally long.

42. An implantable cardiac stimulation device, comprising:
a physiological sensor that detects a physiologic parameter associated with a diurnal state of the patient;
a QT measuring circuit that measures a QT interval based on at least one of an evoked cardiac event or an intrinsic cardiac event;
a pulse generator that delivers pacing pulses to at least one chamber of the patient's heart at an adjustable pacing rate; and
a control circuit connected to the physiological sensor, pulse generator, and to the QT measuring circuit, wherein the control circuit is operative to process the physiological parameter to determine the diurnal state, and that is operative to determine when the measured QT interval is abnormally long for the diurnal state, and that is operative to adjust the pacing rate to shorten the QT interval to within a normal range;
wherein the control circuit verifies that V—V timing is optimized before assessing whether the QT interval is abnormally long.

43. An implantable cardiac stimulation device, comprising:
- a physiological sensor that detects a physiologic parameter associated with a diurnal state of the patient;
- a QT measuring circuit that measures a QT interval based on at least one of an evoked cardiac event or an intrinsic cardiac event;
- a pulse generator that delivers pacing pulses to at least one chamber of the patient's heart at an adjustable pacing rate; and
- a control circuit connected to the physiological sensor, pulse generator, and to the QT measuring circuit, wherein the control circuit is operative to process the physiological parameter to determine the diurnal state, and that is operative to determine when the measured QT interval is abnormally long for the diurnal state, and that is operative to adjust the pacing rate to shorten the QT interval to within a normal range;
- wherein the QT interval is the difference between a QT interval of one of the ventricles of the heart and a corresponding QT interval of the other one of the ventricles of the heart.

44. An implantable cardiac stimulation device, comprising:
- a physiological sensor that detects a physiologic parameter associated with a diurnal state of the patient;
- a QT measuring circuit that measures a QT interval based on at least one of an evoked cardiac event or an intrinsic cardiac event;
- a pulse generator that delivers pacing pulses to at least one chamber of the patient's heart at an adjustable pacing rate; and
- a control circuit connected to the physiological sensor, pulse generator, and to the QT measuring circuit, wherein the control circuit is operative to process the physiological parameter to determine the diurnal state, and that is operative to determine when the measured QT interval is abnormally long for the diurnal state, and that is operative to adjust the pacing rate to shorten the QT interval to within a normal range;
- wherein the QT interval is the difference between a stim-T interval of one of the ventricles of the heart and a corresponding stim-T interval of the other one of the ventricles of the heart.

45. An implantable cardiac stimulation device, comprising:
- a physiological sensor that detects a physiologic parameter associated with a diurnal state of the patient;
- a QT measuring circuit that measures a QT interval based on at least one of an evoked cardiac event or an intrinsic cardiac event;
- a pulse generator that delivers pacing pulses to at least one chamber of the patient's heart at an adjustable pacing rate; and
- a control circuit connected to the physiological sensor, pulse generator, and to the QT measuring circuit, wherein the control circuit is operative to process the physiological parameter to determine the diurnal state, and that is operative to determine when the measured QT interval is abnormally long for the diurnal state, and that is operative to adjust the pacing rate to shorten the QT interval to within a normal range;
- wherein the QT interval is the difference between a J-T interval of one of the ventricles of the heart and a corresponding J-T interval of the other one of the ventricles of the heart.

46. An implantable cardiac stimulation device, comprising:
- a physiological sensor that detects a physiologic parameter associated with a diurnal state of the patient;
- a QT measuring circuit that measures a QT interval based on at least one of an evoked cardiac event or an intrinsic cardiac event;
- a pulse generator that delivers pacing pulses to at least one chamber of the patient's heart at an adjustable pacing rate; and
- a control circuit connected to the physiological sensor, pulse generator, and to the QT measuring circuit, wherein the control circuit is operative to process the physiological parameter to determine the diurnal state, and that is operative to determine when the measured QT interval is abnormally long for the diurnal state, and that is operative to adjust the pacing rate to shorten the QT interval to within a normal range;
- wherein the control circuit increases the pacing rate when a measured QT interval exceeds a QT Threshold; and
- wherein the control circuit maintains the pacing rate at an increased rate for a period of time after the QT interval falls below the QT Threshold.

47. An implantable cardiac stimulation device for treating abnormal ventricular activation-recovery time, comprising:
- means for detecting a patient's diurnal state including at least a sleep and an awake state;
- means for measuring QT intervals based on at least one of an evoked cardiac event or an intrinsic cardiac event;
- pulse generating means for generating pacing pulses to control a pacing interval of the pacing pulses;
- control means, in response to the measuring means, for adjusting the pacing interval by an amount that sufficiently shortens the QT interval to maintain the QT interval to within a normal range for the detected diurnal state;
- means for using a QT sleep threshold as the QT Threshold when the patient is in a sleep state; and
- means for using a QT awake threshold as the QT Threshold when the patient is in an awake state;
- wherein the control means varies the pacing interval when a measured QT interval exceeds a QT Threshold.

48. The device of claim 47, wherein:
- the control means further provides closed loop control by adjusting the pacing interval in an opposite direction of the measured QT interval.

49. The device of claim 47, further comprising:
- means for storing the QT sleep threshold and the QT awake threshold based on the patient's QT intervals measured during the sleep and wake states, respectively.

50. The device of claim 47, further comprising:
- means for verifying that capture is maintained in at least one ventricle before assessing whether the QT interval is abnormally long.

51. The device of claim 47, further comprising:
- means for verifying that capture is maintained in both ventricles before assessing whether the QT interval is abnormally long.

52. The device of claim 47, further comprising:
- means for verifying that V—V timing is optimized before assessing whether the QT interval is abnormally long.

53. A method for treating abnormal ventricular activation-recovery time using an implantable cardiac stimulation device, comprising:

detecting a diurnally varying parameter of the patient;

correlating the patient's diurnally varying parameter to an activity state including at least a sleep and an awake state;

measuring QT intervals based on at least one of an evoked cardiac event or an intrinsic cardiac event during the sleep and awake states;

generating pacing pulses to control a pacing interval of the pacing pulses;

adjusting the pacing interval by an amount that sufficiently shortens the QT interval to maintain the QT interval to within a normal range for the detected activity state;

defining a QT sleep threshold as the QT Threshold when the patient is in a sleep state; and defining a QT awake threshold as the QT Threshold when the patient is in an awake state;

wherein the adjusting step comprises shortening the pacing interval when a measured QT interval exceeds a QT Threshold.

54. The method of claim 53, wherein the adjusting step comprises:

controlling the pacing interval in a closed loop manner by adjusting the pacing interval in an opposite direction of the measured QT interval.

55. The method of claim 53, further comprising:

learning the QT sleep threshold and the QT awake threshold based on the patient's QT intervals measured during the sleep and wake states, respectively; and updating the QT sleep threshold and the QT awake threshold in a memory.

56. The method of claim 53, further comprising:

verifying that capture is maintained in at least one ventricle before assessing whether the QT interval is abnormally long.

57. The method of claim 56, further comprising;

verifying that capture is maintained in both ventricles before assessing whether the QT interval is abnormally long.

58. The method of claim 53, further comprising:

verifying that V—V timing is optimized before assessing whether the QT interval is abnormally long.

* * * * *